United States Patent
Joshi et al.

(10) Patent No.: US 11,089,962 B2
(45) Date of Patent: Aug. 17, 2021

(54) PATIENT MONITORING SYSTEM AND METHOD WITH VOLUME ASSESSMENT

(71) Applicant: General Electric Company, Schenectady, NY (US)

(72) Inventors: Bhuvnesh Joshi, Bangalore (IN); Ravi Jaiswal, Bangalore (IN)

(73) Assignee: General Electric Company, Schenectady, NY (US)

( * ) Notice: Subject to any disclaimer, the term of this patent is extended or adjusted under 35 U.S.C. 154(b) by 969 days.

(21) Appl. No.: 15/670,842

(22) Filed: Aug. 7, 2017

(65) Prior Publication Data

US 2019/0038146 A1  Feb. 7, 2019

(51) Int. Cl.
| | | |
|---|---|---|
| *A61B 5/0205* | (2006.01) | |
| *A61B 5/00* | (2006.01) | |
| *G16H 40/63* | (2018.01) | |
| *G06F 1/16* | (2006.01) | |

(52) U.S. Cl.
CPC ........ *A61B 5/02055* (2013.01); *A61B 5/0024* (2013.01); *A61B 5/7405* (2013.01); *G16H 40/63* (2018.01); *A61B 5/7445* (2013.01); *A61B 2560/0242* (2013.01); *G06F 1/1613* (2013.01)

(58) Field of Classification Search
USPC .................. 381/26, 56, 57, 71.14, 107, 108
See application file for complete search history.

(56) References Cited

U.S. PATENT DOCUMENTS

| | | | |
|---|---|---|---|
| 5,450,494 A * | 9/1995 | Okubo | ..................... H03G 3/32 348/E5.122 |
| 6,529,605 B1 | 3/2003 | Christoph | |
| 7,606,376 B2 | 10/2009 | Eid et al. | |
| 7,908,134 B1 | 3/2011 | Felber | |
| 2010/0041975 A1 | 2/2010 | Chen et al. | |
| 2011/0224507 A1* | 9/2011 | Banet | .................... H04W 4/029 600/301 |
| 2012/0071741 A1 | 3/2012 | Moussavi et al. | |
| 2015/0209583 A1* | 7/2015 | Pitts | ................... A61N 1/36031 607/48 |
| 2017/0064470 A1* | 3/2017 | Popovac | ............. H04M 1/7253 |
| 2018/0376237 A1* | 12/2018 | Schlesinger | ......... H04R 1/1083 |

FOREIGN PATENT DOCUMENTS

| | | |
|---|---|---|
| JP | 2004-537335 A | 12/2004 |
| JP | 2011-212167 A | 10/2011 |

OTHER PUBLICATIONS

International Search Report and Written Opinion issued in connection with corresponding PCT Application No. PCT/US2018/039298 dated Oct. 19, 2018, 11 pages.

* cited by examiner

*Primary Examiner* — Yosef K Laekemariam
(74) *Attorney, Agent, or Firm* — Andrus Intellectual Property Law, LLP

(57) ABSTRACT

A patient monitoring device includes a microphone, a speaker, a display, a processor, and a volume assessment module executable on the processor to operate the microphone to generate an audio environment recording of the audio environment surrounding the patient, determine an ambient noise level based on the audio environment recording, and control the speaker and/or display of the patient monitoring device based on the ambient noise level.

16 Claims, 6 Drawing Sheets

PATIENT MONITORING SYSTEM AND METHOD WITH VOLUME ASSESSMENT

BACKGROUND

The present disclosure relates generally to medical devices and, more specifically, to medical monitoring devices for monitoring a patient's physiology and health status.

In the field of medicine, physicians often desire to continuously monitor one or more physiological characteristics of a patient. Such patient monitoring may involve the use of several separate monitoring devices simultaneously, such as a pulse oximeter, a blood pressure monitor, a heart monitor, a temperature monitor, etc. Multi-parameter monitors are also available where different sensor sets may be connected to a single monitor. Such patient monitors are becoming more portable and mobile, giving capabilities to caregivers to provide continual physiological monitoring in various environments where a patient is being treated, in when moving the patient between treatment locations.

SUMMARY

This Summary is provided to introduce a selection of concepts that are further described below in the Detailed Description. This Summary is not intended to identify key or essential features of the claimed subject matter, nor is it intended to be used as an aid in limiting the scope of the claimed subject matter.

In one embodiment, a patient monitoring device includes a microphone, a speaker, a display, a processor, and a volume assessment module executable on the processor to operate the microphone to generate an audio environment recording of the audio environment surrounding the patient, determine an ambient noise level based on the audio environment recording, and control the speaker and/or display of the patient monitoring device based on the ambient noise level.

In one embodiment, a method of controlling a patient monitoring device, wherein the patient monitoring device has at least a microphone and a speaker, includes operating the microphone to generate an audio environment recording, and determining an ambient noise level based on the audio environment recording. The audio environment recording is filtered to remove an alarm frequency of the patient monitoring device, and then at least one decibel level is measured based on the filtered audio environment recording. The method further includes comparing the decibel level to one or more noise level thresholds to determine an ambient noise level, and determining a desired volume setting for audio alerts by the speaker based on the ambient noise level. The volume setting for the speaker is then automatically adjusted based on the desired volume setting.

In another embodiment, a method of controlling a patient monitoring device having at least one microphone and at least one speaker, includes operating the microphone to generate an audio environment recording, determining an ambient noise level based on the audio environment recording, filtering the audio environment recording to remove an alarm frequency of the patient monitoring device, and measuring at least one decibel level based on the filtered audio environment recording. The decibel level is then compared to one or more noise level thresholds to determine an ambient noise level, and a visual noise indicator is generated on a display based on the ambient noise level.

BRIEF DESCRIPTION OF THE DRAWINGS

The present disclosure is described with reference to the following Figures.

DETAILED DESCRIPTION

Figure 1:
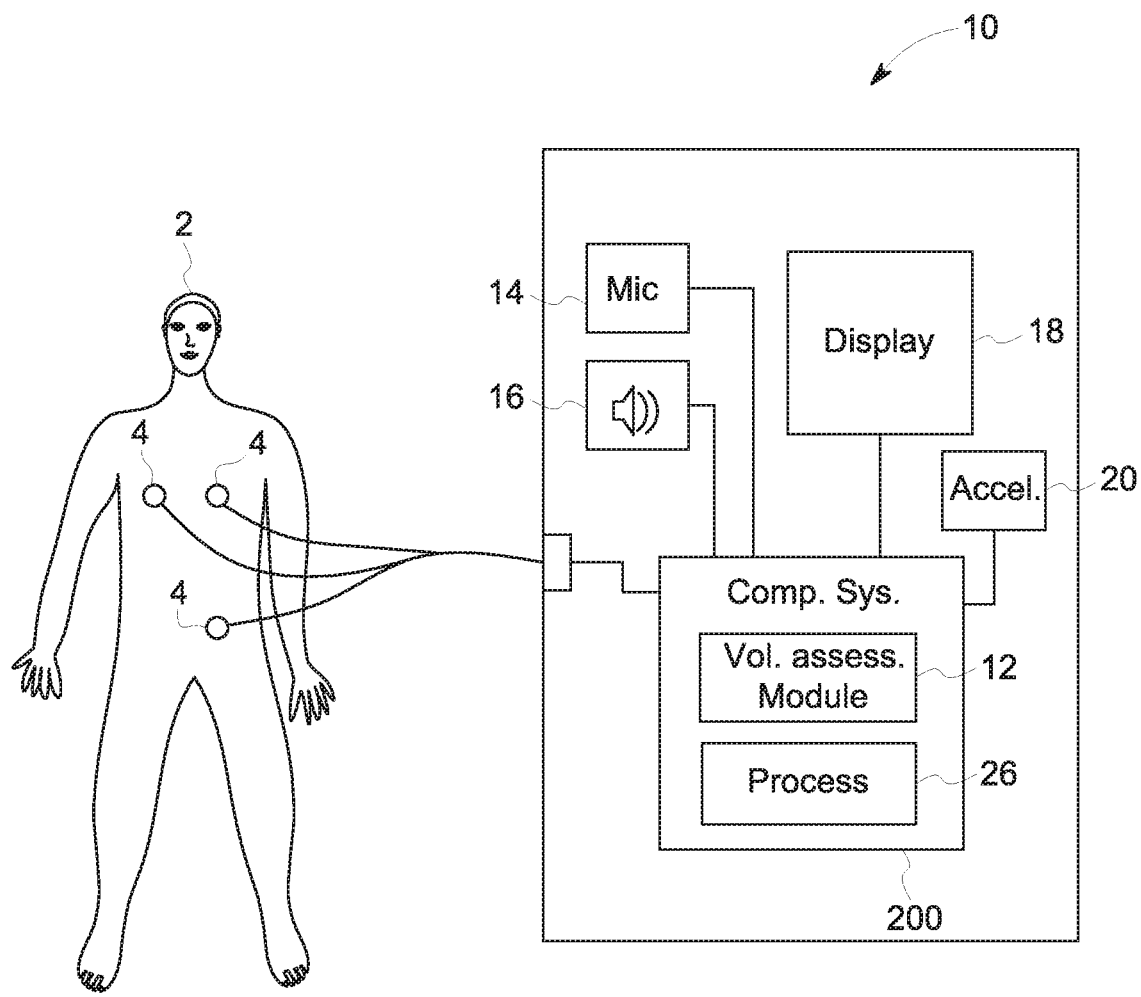
FIG. 1 is a schematic diagram depicting one embodiment of a patient monitoring device having a volume assessment module.

Given their portability, patient monitoring devices must operate in a number of different noise conditions, yet their alarm generation means and modes remain the same. The inventors have recognized that alarm generation by mobile medical devices, especially patient monitoring devices, can be inappropriate based on the context and the environment of the patient. For example, in a quiet and dark environment, an audio and/or visual alarm may be too loud and thus be disruptive to the patient, surrounding patients or family members, and/or to caregivers. To provide just one example, noise and light levels are often controlled in neonatal care environments, where multiple infant patients are often being cared for in the same room. Thus, the volume of audio alarms is typically kept to a minimum. However, incubators and other infant care devices are portable, and infants may be moved to various environments for care which may have high ambient noise. The quiet alarms set for the neonatal care environment is likely too quiet to be readily noticed in a louder and busier environment, and thus alarms could go unnoticed, failing to adequately alert clinicians to an alarm condition or technical malfunction. Thus, patient monitoring devices where the alarming is set at a low volume, such as for operation in a neonatal care unit, may fail to sufficiently alert clinicians to an important event when the infant and patient monitoring device are in a different environment. Similarly, patient monitoring devices where the alarming is set to have a high volume, such as for operation in an emergency room, will likely be too loud for other environments and may be unnecessarily disruptive in other, quieter, environments.

In view of the foregoing problems and challenges recognized by the inventors, the present system and method were developed where one or more patient monitoring devices associated with the patient detect ambient noise and adjust alarm volume levels to account for and adapt to the environment of the patient. With reference to the example of FIG. 1, the patient monitoring device 10 may utilize a microphone 14 to record the audio environment surrounding a patient 2 and process the audio recordings by the microphone to determine an ambient noise level. For example, the patient monitoring device 10 may include software, including a volume assessment module 12, that continuously receives and assesses a digital audio signal of the audio environment recording by the microphone 14 near the patient 2, isolates the ambient noise in the audio environment recording, and then classifies the ambient noise level as either low, medium, or high. In other embodiments, the audio processing software may process the audio signal in predetermined time increments to periodically generate an ambient noise level indicator, which may be a visual indicator provided on the display 18 associated with the patient monitoring device 10, or may be an audio alert provided by the speaker 16. In still other embodiments, the volume assessment module 12 may only monitor the ambient noise level upon the occurrence of certain events. For example, the volume assessment module 12 may activate the ambient volume controls when the patient monitor is being moved, which could indicate that the patient is being moved from one care environment to another.

In the exemplary embodiment schematically depicted in FIG. 1, a patient monitoring device 10 receives physiological signals from sensors 4 connected to the patient 2. In the depicted embodiment, the sensors 4 are ECG electrodes recording cardiac electrical activity and the patient monitor is an electrocardiograph (ECG). In other embodiments, the patient monitoring device 10 may be any type of patient monitor—i.e., monitoring any type of physiological information about the patient, or multiple types of physiological information. To provide just a few other examples, the patient monitoring device 10 may be, or include, a blood pressure monitor, a pulse oximeter, an electroencephalograph (EEG), a temperature monitor, or the like.

The patient monitoring device 10 receives the physiological data sensed by the sensors 4 and processes the data to determine the physiological condition of the patient 2. As is well known in the relevant art, the patient monitoring device 10 may include computer software executable on the processor 26 to compare the physiological data to alarm levels based on predefined alarm limits, and to generate alarms when those alarm limits are exceeded. The alarm may then be enunciated by one or more speakers 16 associated with the patient monitoring device 10. The speakers have a controllable volume, which is controlled according to a volume setting. In certain embodiments, the patient monitoring device 10 may allow various volume settings to be established, including a volume setting specific to patient alarms. The volume setting may be user-controllable value, which may be inputted via any user interface associated with the patient monitoring system 10, such as via the display 18 (where the display 18 is a touch screen display), or via other user interface means, such as buttons, analog dials, etc.

The patient monitoring device 10 includes a microphone 14 configured to enable recording of an audio environment surrounding the patient monitor 10 and/or the patient 2. The patient monitoring device 10 further includes a speaker 16 capable of enunciating alerts and/or alarms, such as to alert a clinician to a change in the patient's physiological condition and/or a technical problem with the patient monitoring device 10, the sensors 4, etc. The patient monitoring device 10 further includes a display 18, which may be any type of display device, such as, but not limited to, a light-admitting diode display (LED), a liquid crystal display (LCD), an electroluminescent display (ELD), a plasma display panel, or the like. In the depicted embodiment, the display 18 and the speaker system are controlled by the computing system 20, and are connected thereto by wired or wireless communication links. In other embodiments, additional and dedicated control devices may be associated with the display 18 and/or the speaker 16, which may cooperate with the computing system 200 in order to carry out control instructions of those devices, such as according to the methods described herein.

In certain embodiments, the patient monitoring device 10 may be a central hub, or central monitoring control device for multiple different patient monitoring devices monitoring different physiological signals from the patient. In such an embodiment, the central patient monitoring device 10, and the volume assessment module 12 therein, may assess and control volume settings for multiple different patient monitoring devices which may each have their own speaker and separate alarming control. In such an embodiment, the computing system 200 of the central patient monitoring device 10 may communicate with the various networked or associated patient monitoring devices, including by wired or wireless means.

The patient monitoring system 10 may further include an accelerometer 20 configured to measure motion of the patient monitoring device 10. For example, the accelerometer may generate motion data based on the measured acceleration in one or more axes. For example, the accelerometer 20 may be a three-axis accelerometer. In other embodiments, motion may be measured by a combined gyroscope-accelerometer, which allows movement and orientation tracking. In still other embodiments, movement of the patient monitor 10 may be measured by a sensor capable of acting as an accelerometer and/or gyroscope.

In one embodiment, the computing system 20 receives motion data 30 from the accelerometer and compares the motion data to one or more thresholds for detecting movement of the patient monitoring device 10. For example, the volume assessment module 12 may determine whether the motion data exceeds a threshold magnitude. Alternatively or additionally, the volume assessment module 12 may determine whether the motion data 30 exceeds a threshold magnitude, or otherwise has a nonzero value, for at least a predetermined amount of time indicating that the patient monitoring device 10 is being moved. Upon detecting motion of the patient monitoring device 10, the volume assessment module may then operate to assess the ambient noise level and whether current volume settings for the speaker 16 are appropriate based on the ambient noise level.

The volume assessment module 12 includes software instructions executable on a processor 26 to operate the microphone 14 to generate an audio environment recording 32. The volume assessment module 12 includes sound level logic for isolating ambient noise and comparing the isolated ambient noise to thresholds in order to determine the ambient noise level 36. For example, the ambient noise may be a decibel (dB) relative to a reference pressure, such as 20 micropascals. For example, ambient noise levels may be measured using a frequency weighting filter which weights certain frequencies expected in the background noise of a medical environment and discounts less relevant frequencies, such as those on the fringe of the human auditory spectrum or those inhabited by non-ambient noise generators. For example, the frequency weighting filter may be an A-weighting scale, and the resulting decibel level measurements of the audio environment recording may be denoted as decibels on the A-weighting scale dB (A).

In one embodiment, the volume assessment module 12 may be configured to filter out non-ambient noise, such as noise coming from the patient monitoring device 10 or other patient monitoring devices associated with the patient 2. The patient monitoring device 10 may have one or more alarming frequency ranges at which the speaker 16 generates various alarms and alerts. To provide just one example, the patient monitoring device 10 may have an alarm frequency range of 100 Hz to 3.0 KHz, and the volume assessment module 12 may filter out that frequency range from the audio environment recording 32 prior to determining the ambient decibel level. Thereby, the volume assessment module 12 can avoid including the alarms from the patient monitoring device in the ambient noise assessment, and thus avoid engaging in a feed back loop of continuously increasing the volume setting to overcome the ambient noise level and, in turn, increasing the measured ambient noise level.

In one embodiment, the volume assessment module 12 compares the ambient decibel level to one or more noise level thresholds in order to select an ambient noise level. To provide just one example, the volume assessment module 12 may select from a low, medium, and high ambient noise level, where any value below a first noise level threshold is deemed a "low ambient noise level," anything above a second noise level threshold is deemed a "high ambient noise level," and anything between the first and second noise level thresholds is deemed a "medium ambient noise level." To provide an explanatory example, the first noise level threshold may be 30 dB(A), and the second noise level threshold may be 40 dB(A). In various embodiments, the volume assessment module 12 may automatically determine a volume setting for the speaker 16 based on the ambient noise level 36, or it may provide volume adjustment indicators on the display 18 instructing a user on how to adjust the volume setting to an appropriate level based on the ambient noise level 36. In embodiments where the volume assessment module 12 automatically adjusts the volume setting, a desired volume setting 39 may be associated with each ambient noise level 36. Accordingly, the volume assessment module 12 may adjust one or more of the volume settings for the speaker based on the desired volume setting 39. The volume assessment module 12 may continually assess the ambient noise level 36 and determine a desired volume setting 39 accordingly, and thus any alarm enunciation by the speaker 16 will automatically by generated at an appropriate volume based on the audio environment of the patient 2.

Figure 3:
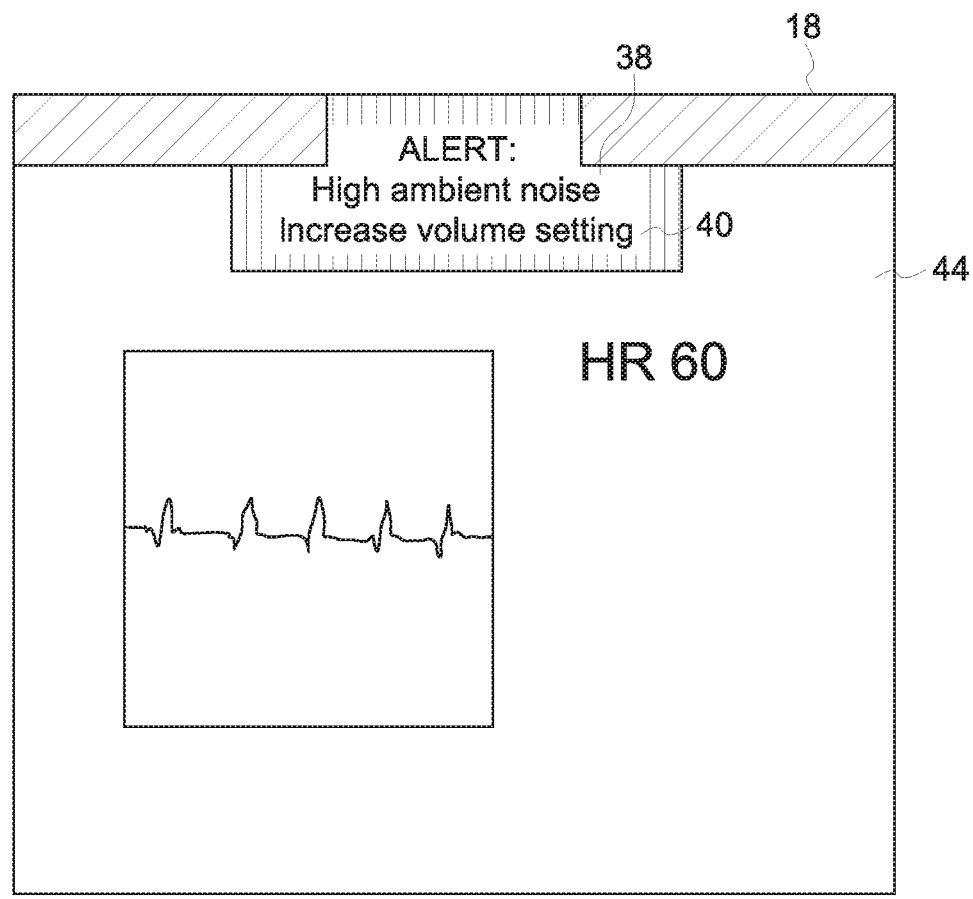
FIG. 3 depicts and exemplary display screen of a patient monitoring device having a volume assessment module.

In other embodiments, the volume adjustment may not be automatic and the volume assessment module 12 may instead alert a clinician to a change in ambient noise level 36 and/or instruct an appropriate volume adjustment by providing an adjustment indicator 40. FIG. 3 depicts an exemplary embodiment of a display screen 44 on a display 18 providing a visual noise indicator 38. The display screen 44 provides a visual display containing information about the patient's physiological condition and/or the monitored physiological parameter, as well as information about the patient monitoring device itself. For example, the visual noise indicator 38 and/or adjustment indicator 40 may be provided along a top portion of the display screen 44 as exemplified in FIG. 3. In certain embodiments, the visual noise indicator 38 and/or the adjustment indicator 40 may be provided in a dedicated area of the display screen 44 dedicated to provide technical alarms and/or other technical information about the patient monitoring device 10.

In other embodiments, the visual noise indicator 38 may be provided on a separate display than that providing information regarding physiological parameters and/or other user interface elements. For example, the visual noise indicator 38 may be a dedicated visual indicator, such as an indicator light or a small digital display dedicated to displaying the ambient noise level 36, the desired volume setting 39, and/or the adjustment indicator 40. To provide just one example, the visual noise indicator could be an LED indicator light that illuminates when the current volume setting for the speaker 16 is inappropriate based on the detected ambient noise level. For example, the indicator light could illuminate in a first color when the current volume setting is too high, and illuminate in a second color when the current volume setting is too low. In certain embodiments, such as volume assessment systems in incubators and other devices adapted for providing neonatal care, the visual noise indicator 38 may be provided at a location that is not visible to the infant, such as underneath the infant platform projecting onto the ground, or even remotely from the infant care device, such as at a portable device held by the clinician.

In the depicted embodiment, the visual noise indicator 38 provides an alert of "high ambient noise." For example, such a visual noise indicator 38 may be presented on the display screen 44 to alert a user to a change in ambient noise level 36, such as when a current ambient noise level differs from a previously-determined ambient noise level by a threshold change amount. For example, the threshold change amount may be any change in noise level, such as a change between the previously-described low, medium, and high ambient noise levels. Alternatively, especially where the ambient noise level determination has multiple possible values, the threshold change may be a predetermined change amount. Accordingly, when the change in noise level exceeds the threshold, the visual noise indicator 38 may be presented to alert a user to change the volume setting. For example, the volume assessment module 12 may calculate a volume adjustment based on a difference between the desired volume setting 39, which is calculated based on the current ambient noise level 36, and the current volume setting. An adjustment indicator 40 may then be displayed on the display screen 44 in order to instruct a user to carry out the volume adjustment. The adjustment indicator 40 may take any of various forms, providing various specificity to a user on making the volume adjustment. In the example depicted in FIG. 3, the adjustment indicator 40 provides an instruction to "increase volume setting," which is due to the increase in ambient noise level. In certain embodiments, the adjustment indicator 40 may provide more specific instructions to a user, such as what volume setting the volume should be adjusted to, and such an instruction may correspond with the volume setting user interface arrangement (e.g. whether it is a numerical-coded setting, a color-coded setting, or the like). The adjustment indicator 40 may indicate an adjustment direction and/or an adjustment amount for the volume setting, thereby instructing user on the volume adjustment needed in order to reach the desired volume setting 39. For example, the adjustment indicator 40 may include or indicate the desired volume setting 39, instructing the user to make the corresponding volume adjustment. In certain embodiments, the adjustment indicator 40 may be provided as, or as part of, a visual noise indicator 38, or the adjustment indicator 40 may be provided separately (such as in auditory form).

In still other embodiments, the visual noise indicator 38 may be continually shown on the display screen 44 to continually display the ambient noise level 36 and/or the desired volume setting 39 corresponding with ambient noise level 36. In such an embodiment, the visual noise indicator 38 may be periodically updated as changes in the ambient noise level 36 and/or desired volume setting 39 are detected. In other embodiments, the volume assessment module 12 may control the display 18 and/or the speaker 16 to generate an alert that the current volume setting is not appropriate based on the current ambient noise level 36. In still other embodiments, the volume assessment module 12 may control the speaker 16 to provide an auditory alert to the user of a change in the ambient noise level 36, an adjustment indicator 40 instructing a volume adjustment, and/or the desired volume setting 39.

Figure 2:
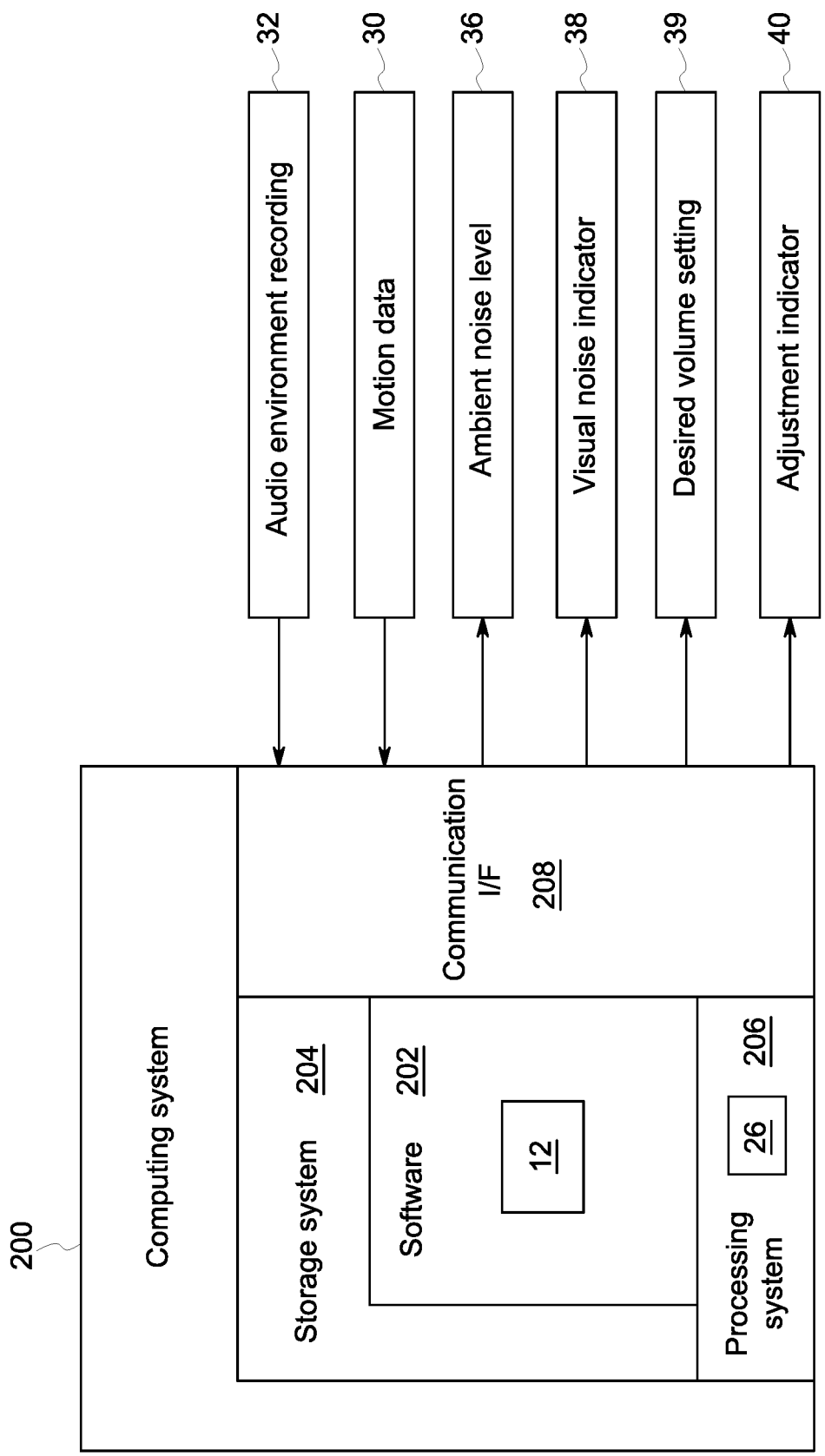
FIG. 2 is a schematic diagram of an exemplary computing system incorporated in or associated with the patient monitoring device.

FIG. 2 provides a system diagram of an exemplary embodiment of the computing system 200 having a volume assessment module 12 executable to provide the control functions described herein. The computing system 200 generally includes a processing system 206, storage system 204, software 202, and a communication interface 208. The processing system 206 loads and executes software 202 from the storage system 204, including the volume assessment module 12, which is an application within the software 202. The volume assessment module 12 includes computer-readable instructions that, when executed by the processing system 206, direct the patient monitoring device 10 to operate as described in the various embodiments disclosed herein.

Although the computing system 200 as depicted in FIG. 2 includes one software 202 encapsulating one volume assessment module 12, it should be understood that one or more software elements having one or more modules may provide the same operation. Similarly, while description as provided herein refers to a computing system 200 and a processing system 206, it is to be recognized that implementations of such systems can be performed using one or more processors, which may be communicatively connected, and such implementations are considered to be within the scope of the description.

The processing system 206 includes the processor 26, which may be a microprocessor, a general purpose central processing unit, an application-specific processor, a microcontroller, or any other type of logic-based device. The processing system 206 may also include circuitry that retrieves and executes software 202 from storage system 204. Processing system 206 can be implemented within a single processing device but can also be distributed across multiple processing devices or sub-systems that cooperate in executing program instructions.

The storage system 204 can comprise any storage media, or group of storage media, readable by processing system 206, and capable of storing software 202. The storage system 204 can include volatile and non-volatile, removable and non-removable media implemented in any method or technology for storage of information, such as computer-readable instructions, data structures, program modules, or other data. Storage system 204 can be implemented as a single storage device but may also be implemented across multiple storage devices or sub-systems. Storage system 204 can further include additional elements, such a controller capable of communicating with the processing system 206.

Examples of storage media include random access memory, read only memory, optical discs, flash memory, virtual memory, and non-virtual memory, magnetic sets, magnetic tape, magnetic disc storage or other magnetic storage devices, or any other medium which can be used to store the desired information and that may be accessed by an instruction execution system, as well as any combination or variation thereof, or any other type of storage medium. Likewise, the storage media may be housed locally with the processing system 206, or may be distributed in one or more servers, which may be at multiple locations and networked, such as in cloud computing applications and systems. In some implementations, the storage media can be a non-transitory storage media. In some implementations, at least a portion of the storage media may be transitory.

The communication interface 208 interfaces between the elements within the computing system 200 and external devices, such as the one or more speakers 16, display 18, microphone 14, accelerometer, and/or any dedicated control system associated therewith, in order to receive the data inputs and provide control outputs described herein.

Figure 4:
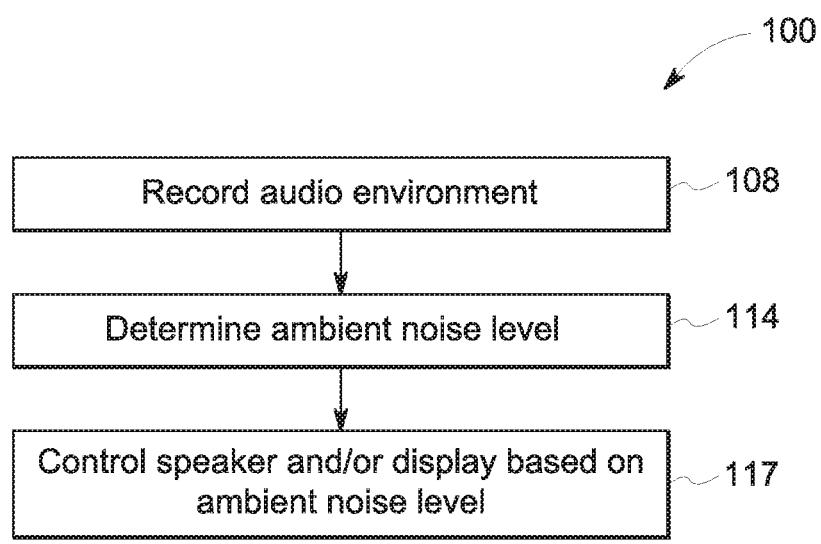
FIG. 4 depicts one embodiment of a method of controlling a patient monitoring device.

FIGS. 4-6B provide exemplary embodiments of methods 100 of controlling a patient monitoring device 10, including control logic and functions embodied in executable software instructions of the volume assessment module 12. As shown in FIG. 4, the volume assessment module 12 operates to record the audio environment 108 via the microphone 14 and to determine the ambient noise level at step 114 based on the audio environment recording. The volume assessment module 12 then controls the speaker 16 and/or the display 18, represented at step 117, based on the ambient noise level determined at step 114. For example, the volume assessment module 12 may control a volume setting for the speaker. Alternatively or additionally, the volume assessment module 12 may control the speaker and/or the display to generate a noise indicator alert and/or to advise a user of a desired volume setting based on the ambient noise level. Various such embodiments are described herein and illustrated with respect to FIGS. 5 and 6A-6B.

Figure 5:
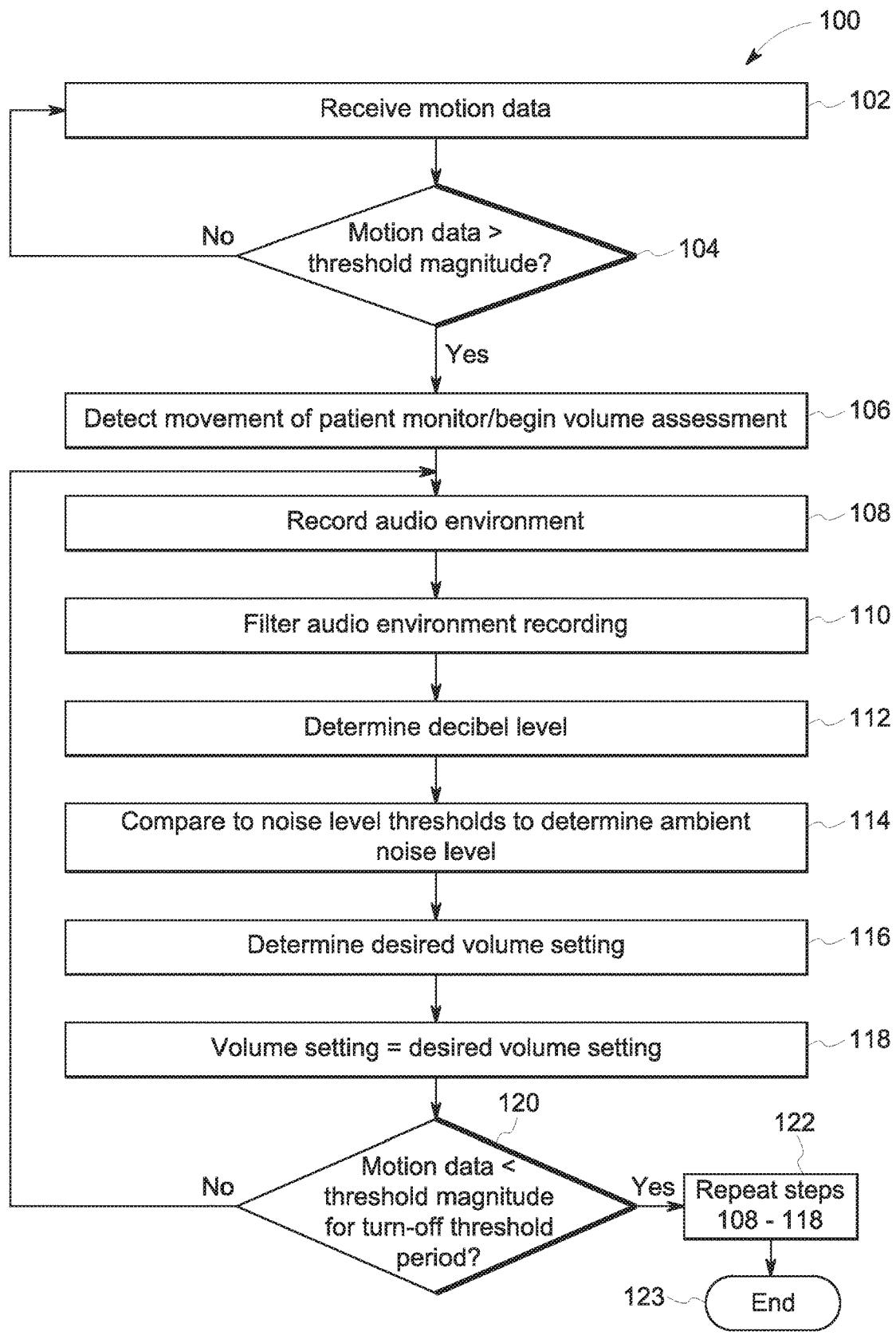
FIGS. 5 and 6A-6B depict additional embodiments of methods of controlling a patient monitoring device.

In the embodiment of FIG. 5, a method 100 of controlling a patient monitoring device 10 includes receiving motion data at step 102 and assessing the motion data, at step 104, to determine whether the motion data exceeds a threshold magnitude. If not, then the patient monitoring device 10 is deemed to be stationary and the system continues to assess the motion data, such as motion data 30 from accelerometer 20, to detect when the patient monitor 10 is moved. Once the motion data exceeds a threshold magnitude at step 104, then movement of the patient monitor is detected and the volume assessment control function is commenced, represented at step 106. Step 108 is executed to record the audio environment via the microphone 14. The audio environment recording is filtered at step 110, such as to remove the alarming frequencies of alarms generated by the patient monitoring device 10. The decibel level of the ambient noise in the audio recording is determined at step 112, such as according to an ambient noise determination algorithm. The decibel level is compared to noise level thresholds in order to determine the ambient noise level at step 114, such as to classify the ambient noise into one of a low, medium, or high ambient noise level. A desired volume setting is determined at step 116 based on the ambient noise level, and a volume setting for alarming by the speaker 16 is set at the desired volume setting at step 118. Once the motion data reflects that the patient monitoring device is no longer moving at step 120, then the volume assessment procedures may be ended. In the depicted example, the patient monitoring device 10 is deemed to not be moving at step 120 once the motion data is less than the threshold magnitude for the turn-off threshold. Once that requirement is met, as represented at step 122, steps 108-118 may then be repeated to determine a final desired volume setting. At that point, the volume assessment algorithm is ended at step 123. In other embodiments, such as that shown in FIGS. 6A-6B, the system may revert back to a previous volume setting set before the volume assessment algorithm commenced. However, the volume assessment module 12 continues to receive and assess the motion data to detect the next movement of the patient monitoring device 10.

Figure 6A:
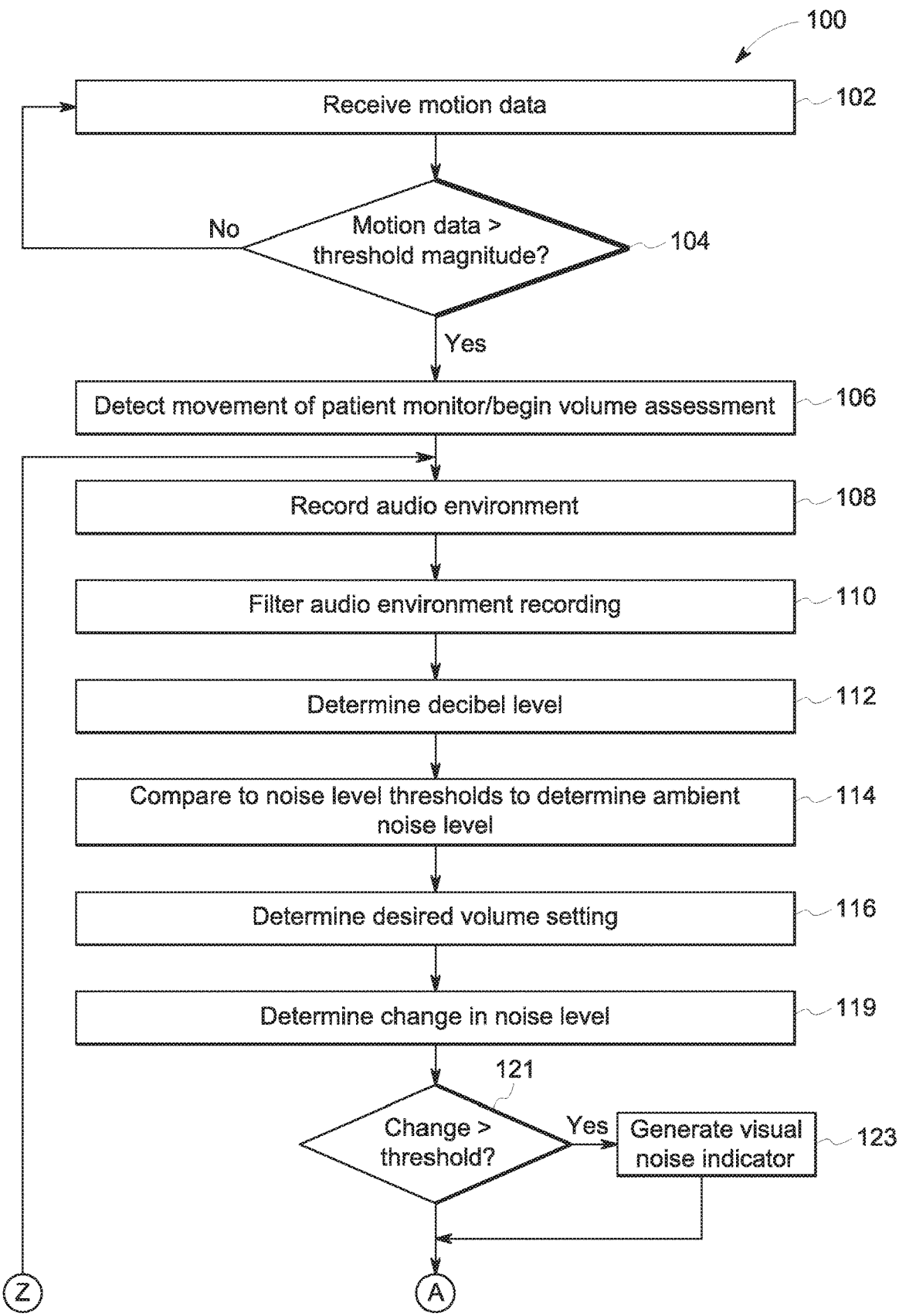
Figure 6B:
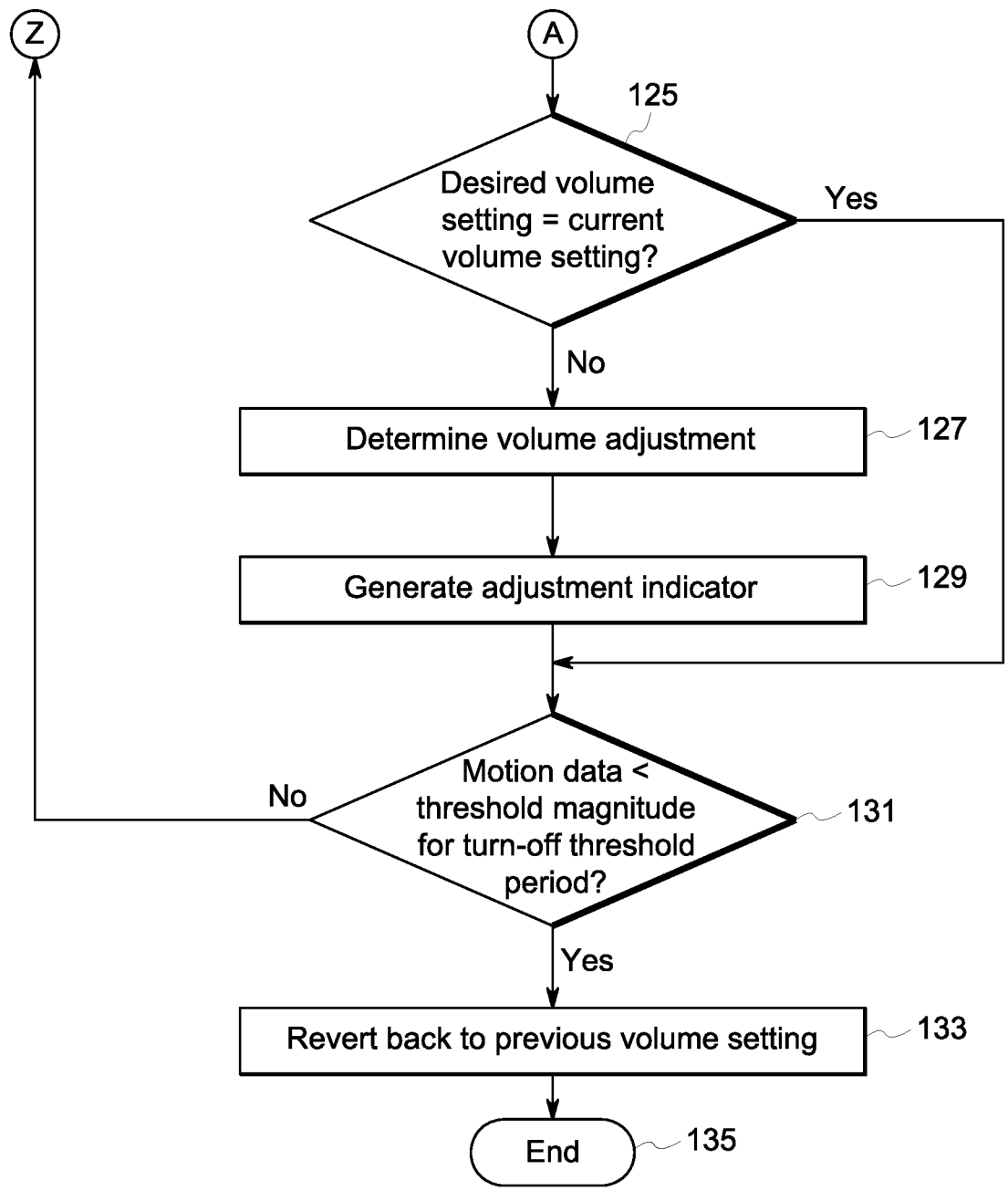

In the method 100 embodiment depicted in FIGS. 6A and 6B, steps 102 through 116 are executed as described above. At step 119, a change in noise level is determined to assess whether a current ambient noise level, determined at step 114, differs from the previously-determined ambient noise level by more than a threshold change amount. If so, then the visual noise indicator is generated at step 123. If the threshold change in noise level is not exceeded, then the method moves to step 125 to determine whether the desired volume setting equals the current volume setting. If not, then a volume adjustment is determined at step 127, and an adjustment indicator is generated at step 129 based on the volume adjustment. For example, the adjustment indicator may be a visual indicator, such as the visual adjustment indicator 40 exemplified and discussed with respect to FIG. 3. Alternatively or additionally, the adjustment indicator may be an auditory indicator or instruction enunciated via the speaker 16.

Whether or not the desired volume setting equals the current volume setting at step 125, step 131 is executed to determine whether the volume assessment algorithm should be terminated, such as whether the motion data has remained less than the threshold magnitude for the turn-off threshold period. If so, then steps 106-129 are re-executed to continue to assess the ambient noise and volume setting. Once the motion stops for at least the turn off threshold period, then the volume assessment algorithm is terminated. In the depicted embodiment, the system reverts back to the previous volume setting at step 133, which is the volume setting for the speaker, or at least the alarming function of the speaker, prior to the initial movement detection of the patient monitor and commencement of the volume assessment. The control algorithm is ended at step 135. However, the volume assessment module 12 continues to receive and assess the motion data to detect the next movement of the patient monitoring device 10.

This written description uses examples to disclose the invention, including the best mode, and also to enable any person skilled in the art to make and use the invention. Certain terms have been used for brevity, clarity and understanding. No unnecessary limitations are to be inferred therefrom beyond the requirement of the prior art because such terms are used for descriptive purposes only and are intended to be broadly construed. The patentable scope of the invention is defined by the claims, and may include other examples that occur to those skilled in the art. Such other examples are intended to be within the scope of the claims if they have features or structural elements that do not differ from the literal language of the claims, or if they include equivalent features or structural elements with insubstantial differences from the literal languages of the claims.

The invention claimed is:

1. A patient monitoring device, comprising:
   a microphone;
   a speaker;
   a display;
   a processor;
   a volume assessment module executable on the processor to:
      operate the microphone to generate an audio environment recording of the audio environment of the patient;
      filter the audio environment recording to remove an alarm frequency of the patient monitoring device;
      measure at least one decibel level based on the filtered audio environment recording;
      compare the decibel level to one or more noise level thresholds in order to determine an ambient noise level;
      determine a desired volume setting for the speaker to generate a patient alarm at the alarm frequency based on the ambient noise level; and
      automatically adjust a volume setting for the speaker to generate the patient alarm based on the desired volume setting.

2. The patient monitoring device of claim 1, further comprising an accelerometer measuring motion of the patient monitoring device to generate motion data;
   wherein the volume assessment module is further executable to, prior to operating the microphone, detect movement of the patient monitoring device based on the motion data.

3. The patient monitoring device of claim 2, wherein the volume assessment module detects movement of the patient monitoring device when the motion data exceeds a threshold magnitude.

4. The patient monitoring device of claim 3, wherein the volume assessment module is further executable to continue generating the audio environment recording and determining the ambient noise level until the motion data is below the threshold magnitude for at least a turn-off threshold period.

5. The patient monitoring device of claim 1, further comprising controlling the display to display a visual noise indicator based on the ambient noise level.

6. The patient monitoring device of claim 5, wherein the volume assessment module is further executable to periodically update the ambient noise level indicator on the display based on the ambient noise level.

7. The patient monitoring device of claim 5, wherein the volume assessment module is further executable to:
   compare a previously determined ambient noise level to a current ambient noise level to determine a change in noise level; and
   display the visual noise indicator based on the current ambient noise level upon detecting a threshold change in noise level.

8. The patient monitoring device of claim 1, wherein the volume assessment module is further executable to:
   determine that a current volume setting for the speaker is inappropriate based on the ambient noise level and/or the desired volume setting.

9. The patient monitoring device of claim 8, wherein the volume assessment module is further executable to determine a volume adjustment based on a difference between the desired volume setting and the current volume setting.

10. The patient monitoring device of claim 9, wherein the volume assessment module is further executable to automatically adjust the current volume setting for the speaker based on the volume adjustment.

11. A method of controlling a patient monitoring device, the patient monitoring device having at least a microphone and a speaker, the method comprising:
    operating the microphone to generate an audio environment recording;
    determining an ambient noise level based on the audio environment recording;
    filtering the audio environment recording to remove an alarm frequency of the patient monitoring device;
    measuring at least one decibel level based on the filtered audio environment recording;
    comparing the decibel level to one or more noise level thresholds to determine an ambient noise level;
    determining a desired volume setting for the speaker to generate a patient alarm at the alarm frequency based on the ambient noise level; and
    automatically adjusting a volume setting for the speaker to generate the patient alarm based on the desired volume setting.

12. The method of claim 11, further comprising:
receiving motion data from an accelerometer measuring motion of the patient monitoring device; and
prior to operating the microphone, detecting movement of the patient monitoring device based on the motion data, wherein detecting movement of the patient monitoring device includes determining that the motion data exceeds a threshold magnitude.

13. The method of claim 12, wherein the volume assessment module continues operating the microphone to generate the audio environment recording and determining the ambient noise level until the motion data is below the threshold magnitude for at least a turn-off threshold period.

14. The method of claim 11, further comprising generating a visual noise indicator on a display based on the ambient noise level.

15. A method of controlling a patient monitoring device, the patient monitoring device having at least a microphone and a speaker, the method comprising:
operating the microphone to generate an audio environment recording;
determining an ambient noise level based on the audio environment recording;
filtering the audio environment recording to remove an alarm frequency of the patient monitoring device;
measuring at least one decibel level based on the filtered audio environment recording;
comparing the decibel level to one or more noise level thresholds to determine an ambient noise level;
comparing a previously determined ambient noise level to a current ambient noise level to determine a change in noise level; and
upon detecting a threshold change in noise level, generating a visual noise indicator on a display based on the ambient noise level.

16. The method of claim 15, further comprising:
determining a desired volume setting for the speaker based on the ambient noise level;
determining a volume adjustment based on a difference between the desired volume setting and a current volume setting;
wherein the visual noise indicator includes an adjustment indicator instructing a user to make the volume adjustment.

* * * * *